United States Patent [19]

Bacha et al.

[11] 4,032,547

[45] June 28, 1977

[54] QUINONE ALKIDE SYNTHESIS SYSTEM

[75] Inventors: John D. Bacha, Monroeville; Joseph S. Matthews, O'Hara Township, County of Allegheny, both of Pa.

[73] Assignee: Gulf Research & Development Company, Pittsburgh, Pa.

[22] Filed: Feb. 23, 1976

[21] Appl. No.: 660,718

[52] U.S. Cl. .......................................... 260/396 N
[51] Int. Cl.² ....................................... C07C 49/64
[58] Field of Search ............................ 260/396 N

[56] References Cited

UNITED STATES PATENTS

| | | | |
|---|---|---|---|
| 3,061,586 | 10/1962 | Thompson | 260/396 N |
| 3,660,505 | 5/1972 | Starnes, Jr. | 260/396 N |
| 3,923,767 | 12/1975 | Kellum et al. | 260/396 N |

OTHER PUBLICATIONS

Dyall et al., J.A.C.S., 94:7 (1972) 2196–2199.

*Primary Examiner*—Vivian Garner

[57] ABSTRACT

A novel and efficient oxidation process for preparing quinone alkides from the corresponding tri-alkyl or phenyl hindered phenols, utilizing ferricyanide as the secondary oxidant in combination with persulfate as the primary oxidant.

11 Claims, No Drawings

QUINONE ALKIDE SYNTHESIS SYSTEM

BACKGROUND OF THE INVENTION

1. Field of the Invention

This invention relates to an oxidation process for preparing quinone alkides from the corresponding trialkyl or phenyl hindered phenols using minor amounts of ferrocyanide or ferricyanide in combination with persulfate in an oxidation-reduction reaction. The quinone alkides are especially suitable for use as polymerization inhibitors for styrene monomer.

2. Description of the Prior Art

It is known that alkaline ferricyanide can be used as an oxidizing agent in combination with other compounds for example, U.S. Pat. No. 3,660,505, Starnes, issued May 2, 1972, teaches the reduction of quinone methides to the corresponding phenols utilizing an alkyl or aralkyl Grignard reagent and the subsequent oxidation of the phenol with basic ferricyanide to produce a new quinone methide, followed by reacting the compound with a tertiary amine or a trialkylphosphine to produce an alkenyl phenol. The resulting product is described as suitable for use as antioxidants for hydrocarbons and especially for polyolefins such as polypropylene.

Filar et al, Tetrahedron Letters, Preparation and Behavior of Simple Quinone Methides, NO. 25, pp. 9–16 (1960), disclose the oxidation of phenols with silver oxide or lead dioxide to produce the quinone methide analog. The reference is primarily a broad overview of the behavior of simple quinone methides, which discloses the stability and reactivity of said quinone methides.

SUMMARY OF THE INVENTION

The present invention encompasses a novel and efficient oxidation process for preparing quinone alkides from the corresponding phenols which comprises contacting in aqueous solution at pH above 7 a minor amount of a soluble iron cyanide salt, a significant amount of a soluble persulfate and a base under conditions suitable for oxidation with a phenol of the formula:

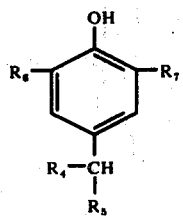

wherein $R_6$ and $R_7$ are either alike or different, members selected from the group consisting of

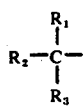

wherein $R_1$, $R_2$ and $R_3$ are either alike or different, members selected from the group consisting of hydrogen, straight or branched chain alkyl moieties having from 1 to 11 carbon atoms; phenyl and alkyl substituted phenyl moieties having up to 9 carbon atoms; alicyclic hydrocarbon moieties having from 3 to 6 carbon atoms, and wherein $R_4$ and $R_5$ are either alike or different, members selected from the group consisting of hydrogen, straight or branched chain alkyl moieties having from 1 to 18 carbon atoms, phenyl and alkyl substituted phenyl moieties having up to 9 carbon atoms, and alicyclic hydrocarbon moieties having from 3 to 6 carbon atoms.

DETAILED DESCRIPTION OF THE INVENTION

The present invention is based on a process for oxidizing hindered phenols to the corresponding quinone alkides; the resulting quinone alkides are useful as polymerization inhibitors for styrene monomer. The oxidation process is carried out by conjointly dispersing and dissolving a phenol-solvent mixture, an iron cyanide compound selected from an oxidant comprising a ferricyanide or a reductant comprising a ferrocyanide in combination with a persulfate and a base in water to provide the desired quinone alkide.

The essential phenols, ferricyanides or ferrocyanides, persulfates and base of the instant invention are described in detail below:

Oxidants

Oxidizing agents which are suitable for use in the present invention include a soluble iron cyanide salt selected from ferrocyanide or ferricyanide in combination with persulfates. It should be understood that during the oxidation-reduction reaction which takes place in the present system, ferrocyanide is oxidized to ferricyanide by the persulfate, and ferricyanide is subsequently reduced to ferrocyanide by the phenol; these oxidation-reduction reactions continue until all the phenol in the reaction vessel is oxidized to quinone alkide, provided that there is sufficient concentration of the ferricyanide and persulfate oxidants initially present. Since ferrocyanide is regenerated to ferricyanide, either can advantageously be used in the initial reaction mixture. It should additionally be noted that persulfate as defined herein is the primary oxidant and ferrocyanide converted to ferricyanide is the intermediate carrier which serves to dehydrogenate the phenol by carrying the primary oxidation potential to the phenol.

Examples of suitable ferricyanides or ferrocyanides include those having sodium, ammonium, potassium, calcium, barium, magnesium, and lithium as the cation, with sodium ferricyanide and sodium ferrocyanide being especially preferred. The oxidizing reactions of the present invention take place with a greater degree of efficiency under alkaline conditions therefore it is highly desirable to add a base to raise the solution pH above 7.

The ferrocyanides of the instant invention are oxidized to ferricyanides by certain persulfates which serve as primary oxidizing agents in the initial reaction. Highly preferred persulfates are selected from the group of sodium persulfate, ammonium persulfate, potassium persulfate, calcium persulfate, barium persulfate, magnesium persulfate, and lithium persulfate, with sodium persulfate being especially preferred. Acidic solutions of the instant composition give poorer yields of quinone alkides; therefore, it is desirable to add a base to maintain the pH above 7. In general, the persulfate is present in the process from about 0.1 mole to 1.5 moles, per mole of phenol, especially from 0.5 mole to 1.2 moles per mole of phenol.

The ferrocyanides are used in the instant process at concentrations of from about 0.01 mole to about 1.0 mole, per mole of phenol, with concentrations of about 0.02 mole to about 0.9 mole, per mole of phenol especially preferred. The ferricyanides are used in the instant process at concentrations of from about 0.01 mole to about 1.0 mole, per mole of phenol, with concentrations of about 0.02 mole to about 0.9 mole, per mole of phenol especially preferred. It should be noted that the concentration of ferrocyanide or ferricyanide in the present process depends to a large extent upon the concentration of phenol present and other variables such as mixing time, temperature, pressure and the like. Thus the concentration of ferrocyanide or ferricyanide can be varied depending upon the above conditions.

For purposes of promoting the reactions between ferrocyanide/persulfate and ferricyanide/phenol, it is especially desirable to use in solution a molar ratio of ferrocyanide or ferricyanide to persulfate of from about 0.02:1 to about 0.9:1 respectively, preferably from about 0.0:1 to about 0.5:1. It should additionally be understood that the concentration of persulfate depends upon the concentration of ferrocyanide or ferricyanide and phenol present in the reaction, and the concentrations of persulfate as well as ferrocyanide or ferricyanide can be varied accordingly.

The following reactions serve to schematically describe the reaction which occurs during the oxidation-reduction of ferrocyanide/ferricyanide and phenol/quinone alkide:

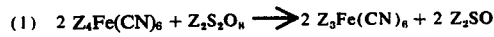

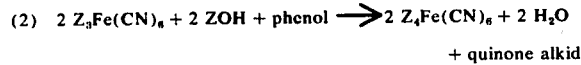

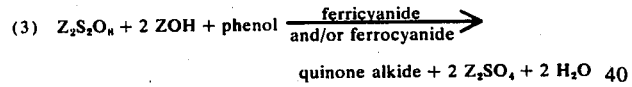

In the above reactions, Z is selected from the group of sodium, potassium, ammonium, calcium, barium, magnesium and lithium or mixtures thereof.

As can be readily determined from the schematic representation above, reaction (1) shows the oxidation of ferrocyanide to ferricyanide by persulfate, while reaction (2) shows the subsequent oxidation of phenol to quinone alkide, and reduction of ferricyanide to ferrocyanide, completing the cycle. Reaction (3) shows the overall oxidation-reduction reaction which occurs in reactions (1) and (2).

Oxidation of Phenol to Quinone Alkide

Phenol, as herein disclosed, is the name given to monohydroxybenzene, but it additionally is the generic name of any hindered tri-alkyl substituted or unsubstituted compound containing one or more hydroxyl groups attached to an aromatic ring.

Quinones are defined as dihydroaromatic compounds or dioxo derivatives thereof, wherein the oxygen atoms occupy positions which are either ortho or para or equivalents in polycyclic compounds to each other. As used herein, quinone alkide means a compound corresponding to the above phenol in which the two, four and six positions on the benzene ring are alkyl or phenyl substituted, with the hydroxy group occupying the number one position.

Normally, the substituted phenol comprises from about 3.0 wt. % to about 15.0 wt. % of the total weight of the components charged to the system, including water and hydrocarbon solvent; and preferably from about 5.0 wt. % to about 10.0 wt. %. Specific examples of phenols which are suitable for use in the instant invention include:

2,6-di-t-butyl-4-methyl phenol;
2,6-di-t-butyl-4-ethyl phenol;
2,6-di-t-butyl-4-n-propyl phenol;
2,6-di-t-butyl-4-isopropyl phenol;
2,6-di-t-butyl-4-n-butyl phenol;
2,6-di-t-butyl-4-iso-butyl phenol;
2,6-di-t-butyl-4-sec-butyl phenol;
2,6-di-t-butyl-4-n-pentyl phenol;
2,6-di-t-amyl-4-methyl phenol;
2,6-di-t-amyl-4-ethyl phenol;
2,6-di-n-dodecyl-4-methyl phenol;
2,6-di-n-dodecyl-4-ethyl phenol;
2,6-di-cyclophentyl-4-methyl phenol;
2,6-di-cyclopentyl-4-ethyl phenol;
2,6-di-cyclohexyl-4-methyl phenol;
2,6-di-cyclohexyl-4-ethyl phenol; and
2,6-di-phenyl-4-methyl phenol.

It is desirable to dissolve the substituted phenol in a solvent, to render it more dispersible in the aqueous solution and to aid the oxidation reaction of the substituted phenol to quinone alkide. Preferred solvents suitable for use include pentane, heptane, hexane, benzene, and toluene, with hexane being especially preferred. The solvent comprises from about 0.1 mole to 20 moles per mole of phenol. The phenols in the instant invention, which are oxidized to quinone alkides, are used to inhibit the polymerization of styrene. The applications of Bacha et al, entitled "Styrene Purification Process", Ser. No. 646,403, filed Jan. 2, 1976, and Bacha et al, entitled "Process for Inhibiting the Polymerization of Styrene", Ser. No. 646,399, filed Jan. 2, 1976, describe suitable processes for use of the quinone alkides and phenols herein disclosed.

Although it is not desired to be bound by any theory, it is believed that the oxidation of phenol to the corresponding quinone alkide proceeds via the formation of intermediate phenoxy radicals which disproportionate to the starting phenol and produce quinone alkide according to the following reactions:

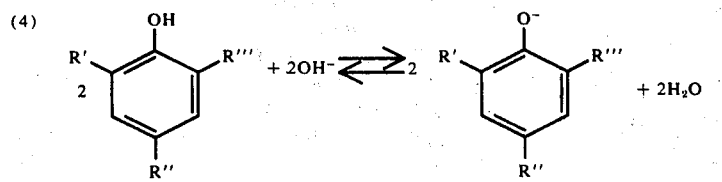

(5)

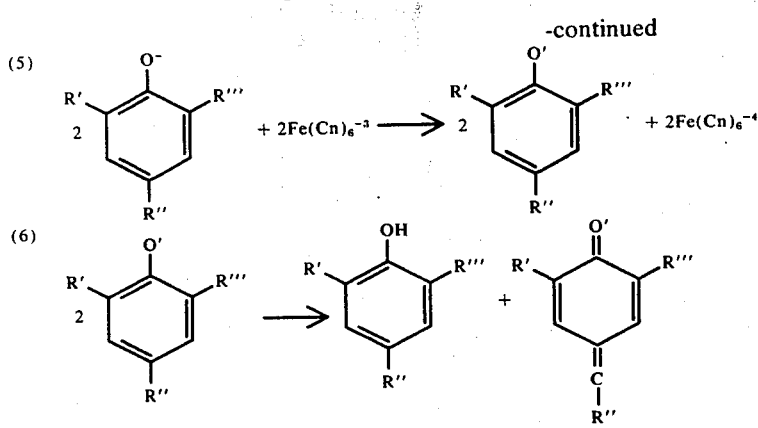

(6)

The overall reaction is represented by reaction (7) below:

(7)

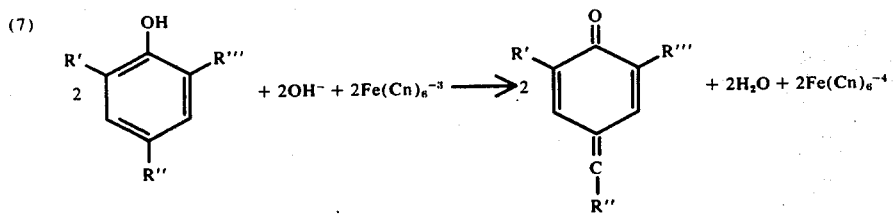

In the above-described reactions, ferricyanide is continuously generated from ferrocyanide by persulfate according to reactions (1); (2) and (3); while ferricyanide oxidizes the phenol to quinone alkide and is concomitantly reduced to ferrocyanide, thus completing the cycle (reactions 4 to 7). Using this system, only minor amounts of ferrocyanide are required.

The Base

The oxidation-reduction reaction of the instant invention preferably takes place in aqueous solution at a pH above 7. Outside this pH range the oxidation performance of the oxidants falls off noticeably. When the solution pH falls below 7, it is desirable to add a base thereto. Bases suitable for use herein include any non-interfering compound which can alter and/or maintain the solution pH within the desired range, and the selection of such compounds can be made by referring to a standard text.

For example, the phosphates, carbonates, bicarbonates or hydroxides which buffer within the pH range of 7 to 12 are useful. Examples of suitable bases include sodium hydroxide, potassium hydroxide, or sodium carbonate. The base is generally used at levels sufficient to keep the solution pH above 7; thus the concentration of base can be varied as needed.

The Oxidizing Process

In its simplest aspect, the method of utilizing the present oxidation process comprises co-mixing an iron cyanide compound selected from ferrocyanide or ferricyanide in an aqueous solution with a mixture consisting of a solvent in combination with a phenol; adding to this mixture an aqueous persulfate, and a base or buffering agent as required.

The compounds in the above process can be added in any order with efficient oxidation results. However, it was discovered that slightly higher yields of quinone alkide are obtained when the persulfate is added to the aqueous solution last. Therefore, in its most preferred mode, persulfate is the last compound added to the aqueous solution.

In particular the oxidation process comprises (a) charging a vessel with water and adding an iron cyanide and base to form an aqueous solution; (b) adding a phenol dissolved in a solvent to the aqueous solution forming a two phase mixture; (c) slowly adding persulfate to the aqueous solution; (d) agitating the mixture for a period sufficient to promote the oxidation of phenol to quinone alkide; and (e) extracting, washing and drying the resultant quinone alkide.

The following examples and tables serve to further illustrate and instruct one skilled in the art the best mode of how to practice this invention and are not intended to be construed as limiting thereof.

EXAMPLES I-XI

Preparation of 2,6-di-t-butyl-4-ethenyl quinone methide

A 5 liter Pyrex Morton flask was charged with 1.625 liters of water and an aqueous solution was prepared by dissolving therein 54 g. (1.35 moles) of sodium hydroxide, and 124 g. (0.256 mole) of sodium ferrocyanide decahydrate. Next, 150 g. (0.64 mole) of 2,6-di-t-butyl-4-ethyl phenol (BHEB) was dissolved in 750 ml. of hexane and the mixture was added to the aqueous solution. The system was concomitantly flushed with nitrogen and agitated. Finally, 165 g. (0.672 mole) of 97 percent sodium persulfate was dissolved in 375 ml. of water and added to the aqueous solution dropwise over a period of 1.8 hours. The temperature of the aqueous solution fluctuated from 27° C. to 33° C. during the aqueous persulfate addition period. The mixture was agitated for an additional 4 hours thereafter.

The resulting system consisted of a lower aqueous phase containing base, ferrocyanide/ferricyanide and persulfate, and an upper phase consisting of hexane, phenol and quinone alkide. The lower aqueous phase was separated and discarded. The upper phase was water washed until neutral and dried over molecular sieves.

A sample of the dried product was analyzed using a Varian aerograph model 1520 gas chromatorgaph equipped with flame ionization detectors and a 5 ft. × ⅛ in. stainless steel column packed with 3 percent SE 30 on 100/120 mesh aeropak 30; the analyses were performed isothermally at 165° C. and 200° C. The results indicated that the reaction product contained 91.1 percent 2,6-di-t-butyl-4-ethenyl quinone methide; 6.3 percent untreated 276-di-t-butyl-4-ethyl phenol; 1.7 percent lower boiling impurities and 0.9 percent higher boiling dimeric products.

The crude 2,6-di-t-butyl-4-ethenyl quinone methide (a yellow crystalline solid) was isolated and purified by stripping the finished product solution of hexane solvent by rotary evaporation followed by recrystallization from 70 ml. of n-hexane. The resulting quinone alkide had a melting point of 92°–94° C. and a purity greater than 95 percent. The experimental results are summarized in Table I and Table II below.

can be substituted for the 2,6-di-t-butyl-4-ethyl phenol with substantially the same results.

EXAMPLE XII

Preparation of 2,6-di-t-butyl-4-n-butenyl quinone methide

A 5 liter Morton flask was charged with 1.5 liters of water; 54.5 g. (1.33 moles) of 97.4 percent sodium hydroxide and 151.5 g. (0.313 mole) of sodium ferrocyanide decahydrate were dissolved therein. The system was next flushed with nitrogen and a mixture of 165.5 g. (0.630) of 2,6-di-t-butyl-4-n-butyl phenol dissolved in 1 liter of hexane was added with agitation to the aqueous solution over a period of 15 minutes. A solution of 161 g. (0.656 mole) of 97 percent sodium persulfate in 0.5 liter of water was added to the system with agitation and under a nitrogen atmosphere over a period of 1.7 hours. The resulting mixture was agitated an additional 4 hours. The reaction temperature fluctu-

TABLE I

Oxidation of BHEB to QE*. Sodium Hydroxide - Sodium Ferrocyanide-Sodium Persulfate System.

| Ex. | Charge | | | NaOH mole | $Na_4Fe(CN)_6^b$ | $Na_2S_2O_8$ | Molar Ratio $Fe(CN)_6^{-4}$/BHEB |
|---|---|---|---|---|---|---|---|
| | $H_2O$ | Hexane | BHEB$^a$ | | | | |
| 1. | 2.0 | 0.75 | 0.640 | 1.35 | 0.256 | 0.672 | 0.4 |
| 2. | 2.0 | 0.75 | 0.640 | 1.35 | 0.128 | 0.672 | 0.2 |
| 3. | 2.0 | 0.75 | 0.640 | 1.35 | 0.064 | 0.672 | 0.1 |
| 4. | 0.5 | 0.15 | 0.128 | 0.269 | 0.051 | 0.127 | 0.4 |
| 5. | 0.5 | 0.15 | 0.128 | 0.269 | 0.128 | 0.127 | 1.0 |
| 6. | 0.5 | 0.15 | 0.128 | 0.269 | 0.128 | 0.127 | 1.0 |
| 7. | 0.5 | 0.15 | 0.128 | 0.269 | 0.128 | 0.127 | 1.0 |

| Run | Combination Method$^c$ | Time$^d$ hrs. | Temp., °C. | mole % BHEB Conversion | QE Yield |
|---|---|---|---|---|---|
| 1. | III | 5.8 | 27–33 | 93.7 | 91.1 |
| 2. | III | 6.3 | 28–34 | 92.9 | 90.6 |
| 3. | III | 6.0 | 28–34 | 80.8 | 78.5 |
| 4. | III | 4.5 | 27–31 | 93.2 | 92.1 |
| 5. | III | 4.5 | 26–30 | 92.5 | 91.4 |
| 6. | II | 5.8 | 25–31 | 90.3 | 88.2 |
| 7. | I | 6.4 | 25–31 | 89.8 | 88.3 |

$^a$BHEB = 2,6-di-t-butyl-ethyl phenol
$^b$decahydrate
$^c$I: sodium hydroxide added to aqueous sodium persulfate - sodium ferrocyanide; then BHEB in hexane added.
II: sodium persulfate added to aqueous alkaline sodium ferrocyanide; then BHEB in hexane added.
III: aqueous sodium persulfate added to mixture of aqueous alkaline ferrocyanide and BHEB in hexane.
$^d$includes solution addition times.
*QE = 2,6-di-t-butyl-ethenyl quinone methide

TABLE II

Oxidation of BHEB to QE*. Mixed Systems.

| Ex. | Charge$^a$ $H_2O$, ml | NaOH | KOH | mole $(NH_4)_2S_2O_8$ | $K_2S_2O_8$ | Molar Ratio$^b$ $OH^-$/BHEB |
|---|---|---|---|---|---|---|
| 8. | 410 | — | 0.268 | 0.128 | — | 2.1 |
| 9. | 410 | — | 0.383 | 0.128 | — | 3.0 |
| 10. | 420 | 0.270 | — | 0.128 | — | 2.1 |
| 11. | 500 | — | 0.282 | — | 0.128 | 2.2 |

| Run | Time, hrs. | Temp., °C. | mole % BHEB Conversion | QE Yield |
|---|---|---|---|---|
| 8. | 6.0 | 25–31 | 74.8 | 74.4 |
| 9. | 6.0 | 22–34 | 69.1 | 68.7 |
| 10. | 5.2 | 23–36 | 76.9 | 76.5 |
| 11. | 5.8 | 25–32 | 92.3 | 91.5 |

$^a$In addition, each run contained 150 ml of hexane, 0.128 mole of BHEB and 0.256 mole of $K_4Fe(CN)_6$.
$^b$Molar ratios of $Fe(CN)_6^{-4}$/BHEB and $S_2O_8^{-2}$/BHEB were constant at 2.0 and 1.0, respectively.
*BHEB = 2,6-di-t-butyl-4-ethyl phenol
QE = 2,6-di-t-butyl-ethenyl quinone methide In the above examples 2,6-di-t-butyl-4-methyl phenol; 2,6-di-t-butyl-4-n-propyl phenol; 2,6-di-t-butyl-4-iso-butyl phenol; or 2,6-di-t-butyl-4-n-pentyl phenol ated from 23° C. to 35° C.

The lower aqueous phase and the upper hexane/quinone alkide phase were separated and the lower aqueous phase was discarded.

The quinone alkide was purified according to Example I and analyzed using a 1520 gas chromatograph equipped with flame ionization detectors and a 5 ft. × 1/8 in. stainless steel column packed with 3 percent SE 30 on 100/120 mesh aeropak 30 at 160° C. and 225° C.

Analysis indicated the resulting product contained 94.4 percent of 2,6-di-t-butyl-4-n-butenyl quinone methide and 5.6 percent of unreacted 2,6-di-t-butyl-4-n-butyl phenol. Lower or higher boiling by-products were not detected. In the example above, 2,6-di-t-amyl-4-methyl phenol or 2,6-di-t-amyl-4-ethyl phenol can be substituted for the 2,6-di-t-butyl-4-n-butyl phenol with substantially the same results.

EXAMPLE XIII

Preparation of 2,6-di-t-butyl-4-sec-butenyl quinone methide

The procedure in Example I was followed with the following exceptions: 56.5 g. (1.37 moles) of 97.4 percent sodium hydroxide; 305 g. (0.630 mole) of sodium ferrocyanide decahydrate; 165.5 g. (0.630 mole) of 2,6-di-t-butyl-4-sec-butyl phenol dissolved in 1 liter of hexane and 161 g. (0.656 mole) or 97 percent sodium persulfate in 0.5 liter of water were added to 1.7 liters of water in a 5 liter Morton flask.

The resulting quinone alkide was separated, purified and analyzed according to Example I. The analysis indicated 88.8 percent of 2,6-di-t-butyl-4-sec-butenyl quinone methide, 9.6 percent unreacted 2,6-di-t-butyl-4-sec-butyl phenol, 0.2 percent lower boiling impurities and 1.4 percent higher boiling impurities. Substantially the same results are obtained when 276-di-n-dodecyl-4-methyl or 2,6-di-n-dodecyl-4-ethyl phenol are substituted for the 2,6-di-t-butyl-4-sec-butyl phenol above. The results of Examples XII, XIII and additional Examples are summarized in Table III.

EXAMPLE XIV

Preparation of 2,6-di-t-butyl-4-isopropenyl quinone methide

The procedure in Example 1 was followed with the following exception 2,6-di-t-butyl-4-isopropyl phenol was substituted for the 2,6-di-t-butyl-4-ethyl phenol.

Analysis of the resulting product indicated 56.6 percent of 2,6-di-t-butyl-4-isopropenyl quinone methide; 34.6 percent unreacted 2,6-di-t-butyl-4-isopropyl phenol and 8.8 percent unknown by-products. When 2,6-di-cyclopentyl-4-methyl phenol; 2,6-di-cyclopentyl-4-ethyl phenol; 2,6-di-cyclohexyl-4-methyl phenol; 2,6-di-cyclohexyl-4-ethyl phenol or 2,6-di-phenyl-4-methyl phenol are substituted for the 2,6-di-t-butyl-4-isopropyl phenol above, substantially the same results are obtained.

EXAMPLE XV

Styrene polymerization inhibition

A 500 ml. flask was charged with 300 g. of styrene and 0.3 g. (1,000 ppm.) of 2,6-di-t-butyl-4-ethenyl quinone methide. A condenser connected to a vacuum system was joined to the flask, the system was flushed with dry nitrogen and the pressure was reduced to 225 mm. Hg. The contents of the flask were at reflux (105° C.) for 3 hours and the pressure was returned to atmospheric by the admittance of nitrogen.

The contents of the flask were added to 500 ml. of methanol, vigorously agitated and allowed to stand for 0.5 hour. The solution was vacuum filtered to separate the methanol insoluble polymer that had formed. Methanol was removed from the polymer by heating in a vacuum oven overnight at a temperature of 90°–100° C. and under a vacuum of 315 mm. of Hg. Analysis indicated only 0.01 g. of styrene was converted to the polymer.

A control sample containing styrene but no quinone alkide was examined according to the procedure above with 31.5 g. of styrene being converted to the polymer.

The quinone alkides as disclosed herein can be substituted in the above example with substantially the same results.

What is claimed is:

TABLE III

Oxidation of 2,6-di-t-butyl-4-alkyl phenols to 2,6-di-t-butyl-4-alkenyl quinone methides

| Ex. | Charge Alkyl Phenol | 1. mole | $H_2O$ | Hexane | NaOH | $Na_4Fe(CN)_6$[a] | $Na_2S_2O_8$ |
|---|---|---|---|---|---|---|---|
| 12 | 2,6-di-t-butyl-4-n-butyl phenol | 0.630 | 2.0 | 1.0 | 1.33 | 0.313 | 0.656 |
| 13 | 2,6-di-t-butyl-4-sec-butyl phenol | 0.630 | 2.2 | 1.0 | 1.37 | 0.630 | 0.656 |
| 14 | 2,6-di-t-butyl-4-iso-propyl phenol | 0.126 | 0.4 | 0.15 | 0.265 | 0.05 | 0.131 |
| 15 | 2,6-di-t-butyl-4-iso-propyl phenol | 0.126 | 0.4 | 0.15 | 0.265 | 0.126 | 0.131 |

| Run | Molar Ratios $OH^-$/ArOH | $Fe(CN)_6^{-4}$/ArOH | $S_2O_8^{-2}$/ArOH | Time, hrs. | Temp., ° C. | Mole % Alkyl Phenol Conversion | Quinone Methide Yield |
|---|---|---|---|---|---|---|---|
| 12 | 2.1 | 0.5 | 1.04 | 5.7 | 25–34 | 94.4 | 94.4[b] |
| 13 | 2.2 | 1.0 | 1.04 | 5.7 | 25–35 | 90.4 | 88.8[c] |
| 14 | 2.1 | 0.4 | 1.04 | 5.1 | 26–31 | 65.4 | 56.6[d] |
| 15 | 2.1 | 1.0 | 1.04 | 5.1 | 26–32 | 86.9 | 77.9[d] |

[a]decahydrate
[b]2,6-di-t-butyl-4-n-butenyl quinone methide
[c]2,6-di-t-butyl-4-sec-butenyl quinone methide
[d]2,6-di-t-butyl-4-iso-propenyl quinone methide 1. A process for preparing quinone alkides from the corresponding phenols which comprises contacting in aqueous solution at pH above 7 a phenol with a minor amount of a soluble iron cyanide salt in the range of about 0.01 mole to 1.0 mole per mole of phenol, a significant amount of a soluble persulfate salt in the range of about 0.1 mole to 1.5 moles per mole of phenol and a base said phenol having the formula:

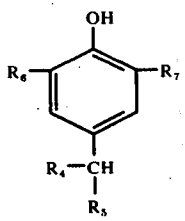

wherein $R_6$ and $R_7$ are either alike or different, members selected from the group of

wherein $R_1$, $R_2$ and $R_3$ are either alike or different, members selected from the group consisting of hydrogen, straight or branched chain alkyl moieties having from 1 to 11 carbon atoms; phenyl and alkyl substituted phenyl moieties having up to 9 carbon atoms; alicyclic hydrocarbon moieties having from 3 to 6 carbon atoms; and wherein $R_4$ and $R_5$ are either alike or different, members selected from the group consisting of hydrogen, straight or branched chain alkyl moieties having from 1 to 18 carbon atoms, phenyl and alkyl substituted phenyl moieties having up to 9 carbon atoms, and alicyclic hydrocarbon moieties having from 3 to 6 carbon atoms, and the molar ratio of iron cyanide salt to persulfate salt being from about 0.02 to about 0.9.

2. The process according to claim 1 wherein the soluble iron cyanide salt is selected from sodium ferrocyanide, ammonium ferrocyanide, potassium ferrocyanide, calcium ferrocyanide, barium ferrocyanide, magnesium ferrocyanide and lithium ferrocyanide.

3. The process according to claim 2 wherein the soluble iron cyanide salt is selected from sodium ferricyanide, ammonium ferricyanide, potassium ferricyanide, calcium ferricyanide, barium ferricyanide, magnesium ferricyanide, and lithium ferricyanide.

4. The process according to claim 3 wherein the soluble persulfate salt is selected from the group of sodium persulfate, ammonium persulfate, potassium persulfate, calcium persulfate, barium persulfate, magnesium persulfate and lithium persulfate.

5. The process of claim 4 wherein the base is selected from sodium hydroxide, potassium hydroxide, or sodium carbonate.

6. The process according to claim 5 wherein the aqueous solution has a pH from about 7 to about 12.

7. The process of claim 6 wherein the phenol is selected from the group of
2,6-di-t-butyl-4-methyl phenol;
2,6-di-t-butyl-4-ethyl phenol;
2,6-di-t-butyl-4-n-propyl phenol;
2,6-di-t-butyl-4-isopropyl phenol;
2,6-di-t-butyl-4-n-butyl phenol;
2,6-di-t-butyl-4-iso-butyl phenol;
2,6-di-t-butyl-4-sec-butyl phenol;
2,6-di-t-butyl-4-n-pentyl phenol;
2,6-di-t-amyl-4-methyl phenol;
2,6-di-t-amyl-4-ethyl phenol;
2,6-di-n-dodecyl-4-methyl phenol;
2,6-di-n-dodecyl-4-ethyl phenol;
2,6-di-cyclopentyl-4-methyl phenol;
2,6-di-cyclopentyl-4-ethyl phenol;
2,6-di-cyclohexyl-4-methyl phenol;
2,6-di-cyclohexyl-4-ethyl phenol; and
2,6-di-phenyl-4-methyl phenol.

8. The process of claim 7 wherein the phenol is deployed in a solvent.

9. The process of claim 8 wherein the solvent is selected from the group of pentane, hexane, heptane, benzene, and toluene.

10. The process according to claim 9 wherein the phenol is in a molar ratio to the solvent of from 0.05:1 to 10:1.

11. The process according to claim 10 wherein the phenol comprises from about 3.0 wt. % to about 15.0 wt. % of the total weight of components charged to the system.

* * * * *